(12) United States Patent
Pfahnl et al.

(10) Patent No.: US 9,717,312 B2
(45) Date of Patent: Aug. 1, 2017

(54) DEVICE FOR REMOVING EARRINGS

(75) Inventors: Andreas C. Pfahnl, Eden Prairie, MN (US); Patrick R. Corneille, Minneapolis, MN (US); Jason R. Gerold, Shakopee, MN (US); Katja U. Pfahnl, Eden Prairie, MN (US)

(73) Assignee: FORTAY JEWELRY PRODUCTS LLC, Eden Prairie, MN (US)

( * ) Notice: Subject to any disclaimer, the term of this patent is extended or adjusted under 35 U.S.C. 154(b) by 742 days.

(21) Appl. No.: 14/111,000

(22) PCT Filed: Apr. 12, 2012

(86) PCT No.: PCT/US2012/033226
§ 371 (c)(1),
(2), (4) Date: Dec. 24, 2013

(87) PCT Pub. No.: WO2012/142226
PCT Pub. Date: Oct. 18, 2012

(65) Prior Publication Data
US 2014/0173902 A1    Jun. 26, 2014

Related U.S. Application Data

(60) Provisional application No. 61/475,891, filed on Apr. 15, 2011.

(51) Int. Cl.
A44C 7/00 (2006.01)
B25B 9/02 (2006.01)
A61B 17/076 (2006.01)

(52) U.S. Cl.
CPC .............. A44C 7/00 (2013.01); B25B 9/02 (2013.01); *A61B 17/076* (2013.01); *Y10T 29/4959* (2015.01)

(58) Field of Classification Search
CPC ......... A44C 7/00; A44C 7/001; A61B 17/076; A61B 17/10; A61B 17/128; B25B 9/02; Y10T 29/4959
See application file for complete search history.

(56) References Cited

U.S. PATENT DOCUMENTS

| | | |
|---|---|---|
| 3,187,751 A | 6/1965 | Coren et al. |
| 4,926,722 A | 5/1990 | Sorensen et al. |
| 5,009,134 A | 4/1991 | Sorensen et al. |
| 5,019,091 A * | 5/1991 | Porat .................. A61B 17/30 606/210 |
| 5,057,078 A | 10/1991 | Foote et al. |

(Continued)

FOREIGN PATENT DOCUMENTS

| | | |
|---|---|---|
| EP | 2 462 968 | 6/2012 |
| JP | 62-52425 | 4/1987 |

(Continued)

*Primary Examiner* — Sarang Afzali
(74) *Attorney, Agent, or Firm* — Kagan Binder, PLLC

(57) ABSTRACT

An earring removal device is provided to remove a stud type earring. The removal device includes tips that easily interface with the earring post and backer to facilitate removal. The tips are coupled to an arcuate structure with a spring characteristic. Simple squeezing of the arcuate structure actuates the tips to separate the backer from the post. The spring characteristic is biased to keep the tips spaced apart, or open, in the absence of a squeezing force.

7 Claims, 17 Drawing Sheets

(56) References Cited

U.S. PATENT DOCUMENTS

| | | |
|---|---|---|
| 5,170,642 A | 12/1992 | Sakata |
| 5,263,968 A * | 11/1993 | Sorensen ............. A61B 17/076 |
| | | 294/99.2 |
| 5,285,703 A | 2/1994 | Carson |
| 5,469,860 A | 11/1995 | De Santis |
| D401,486 S | 11/1998 | Becker |
| 5,830,152 A | 11/1998 | Tao |
| 6,719,735 B1 | 4/2004 | Gammon |
| 7,325,797 B2 | 2/2008 | Kloepfer et al. |
| 7,967,793 B2 | 6/2011 | Sibbitt, Jr. et al. |
| 8,074,340 B2 | 12/2011 | Cicenas et al. |
| 8,512,357 B2 * | 8/2013 | Viola ................. A61B 17/1285 |
| | | 606/142 |
| 2009/0007730 A1 | 1/2009 | Haushalter |
| 2010/0280544 A1 * | 11/2010 | Banks ....................... B25B 9/02 |
| | | 606/210 |
| 2011/0061218 A1 | 3/2011 | Haushalter |

FOREIGN PATENT DOCUMENTS

| | | |
|---|---|---|
| JP | 2001-070015 | 3/2001 |
| WO | WO 2007/003669 | 1/2007 |

* cited by examiner

DEVICE FOR REMOVING EARRINGS

CROSS-REFERENCE TO RELATED APPLICATION

This application claims the benefit from International No. PCT/US2012/033226, which was granted an International filing date of Apr. 12, 2012, which in turn claims the benefit of U.S. Provisional application No. 61/475,891 filed Apr. 15, 2011, titled "Device and Methods for Removing Earrings", which applications are incorporated herein by reference in their entireties.

FIELD OF THE INVENTION

The invention relates generally to devices and methods for removing pierced earrings. More specifically, the present invention relates to devices and methods for removing pierced earrings in which the devices include features that easily interface with the earring and backer to facilitate removal.

BACKGROUND OF THE INVENTION

Earrings and similar jewelry (hereinafter referred to as "earrings" regardless of where the item is worn on the body) may be classed into different types based on how they are attached to the ear or other part of the body. One class of earrings, referred to as "stud earrings", is attached through the ear with a post. The post itself also is referred to as a "stud". Stud earrings are a very common type of earring with a post that penetrates through the ear or other body portion. Stud earrings include an ornamental component attached to the post, typically on the front of the ear (e.g., earlobe) when the stud earring is attached to an ear. Once the post is in place through the body part, a small push-on backer engages with the post, often in a friction fit, to hold the earring in place. A "butterfly" or "butterfly-style" or "butterfly-type" backer, which has two loops extending out from the back of a generally planar plate, is a typical type of backer.

Greater holding force is desirable for expensive and/or heavier earrings so they do not readily fall off. In the case of friction-style backers, larger diameter posts and/or backers are used to provide more resistance or holding force. Another type of push-on backer style that can provide more holding force is a locking backer. A locking backer is similar to a basic push-on design, but the backer snaps into groove(s) in the post. This is one type of snap fit engagement that provides a strong gripping force to retain the backer on the post. Locking backers and associated posts are common with starter stud earrings that are used during an initial piercing. An example of an earring with a locking backer is shown in U.S. Pat. No. 5,170,642.

Typically, an ear is initially pierced with a piercing device often referred to as a "stud gun." These devices provide a large amount of force to rapidly propel the stud through the body part being pierced and connect the stud to the backer in a "gun firing" type action, so that the piercing is quick and relatively painless. Starter stud earrings are intended to remain in the ear for several weeks to be sure the pierced hole does not close (heal shut). A locking backer is often used for starter studs to help ensure the earring does not inadvertently come off. This is particularly a concern for active people and younger children.

The removal of earrings with push-on type backers (locking or standard friction types) is generally done by grabbing the backer with one hand, grabbing the ornamental side with the other hand, and pulling the two apart. For some persons, the removal of stud earrings with push-on or locking backers is extremely challenging, resulting in lengthy times for removal. Push-on backers can require a significant amount of force to remove. The user must pull hard to overcome both the initial static friction and then the dynamic friction to separate the two components. The initial separation force is even higher for locking backers by design (they provide more holding force), where the backer must be pulled from the locking groove(s). A person or child may not have enough finger strength to accomplish this. Removal also may be uncomfortable or even painful.

The ability of a wearer themselves or for another person to remove the backer may be more difficult than desired for several reasons. The relatively large size of any finger and hand, even those of children, compared with the backer size, makes gripping the backer and even some ornamental components difficult. Although the ornamental part can be large enough in some cases for a person to easily grab with their fingers, the backer size is fairly consistent and very small in comparison to a finger. This makes it extremely difficult to grab on to the backer with enough holding power to allow easy separation. Sometimes, a person will attempt to slip their fingernails underneath the plate part of the backer to provide more leverage during separation. In all this, the fingers or fingernails and the pulling action tend to squeeze the earlobe as the person tries to grab more of the earring components. This can be uncomfortable or even painful, especially for a person with a starter stud because the ear tends to be tender from the initial piercing. The problem is further compounded by the fact that the initial separation force may be very high due to the high initial static friction. For example, the backer may not be seated properly (e.g., misaligned) on the post, increasing the friction therebetween. In the case of locking backers, the action of having to get the backer out of the post groove adds to the removal challenge. As a result, the fingers can easily slip during a separation attempt and further irritate the ear.

The backer is typically positioned behind the ear, which makes it difficult to see, particularly when the fingers reach into this small space and further obstruct the view of the backer. Also, a person may have long fingernails, which makes gripping either part of the earring (backer and/or ornamental part) difficult. Another issue that makes earring removal difficult is losing a grip on the backer during separation because the backer is so small and difficult to hold on to during separation. As a result, the backer can fall and, because of its small size, can be difficult to then find. Finally, because of the limited room to gain leverage under the backer, the applied separation forces by the fingers also tend to be highly off axis or not coaxial. So, when the separation does happen, the post may shift sideways after the release from the backer, putting a side load on the earlobe causing further irritation or soreness.

These and other difficulties can make detaching an earring cumbersome, slow, and result in soreness of the earlobe, particularly for wearers of starter stud earrings whose earlobes are already tender from the initial piercing. Therefore, in light of these challenges, it is desirable to have a device that can provide easy separation of friction and locking backer based stud earrings.

One commercially available device intended to make attachment and removal easier is associated with the trade designation "Little Fingers." This device is a simple post with different features on each end. The first end is a straight fork tip for interfacing with a butterfly or loop type backer, and the other end is a fork with dimples to interface with and hold an "earnut" type backer. When removing an earring with this device, the user must still use two hands, their fingers must be used to directly pull on the ornamental end of the earring, and the separation motion is not controlled resulting in jerking, yanking, and/or tugging, possibly making the removal uncomfortable. The "Little Fingers" device also does not provide a means to adequately hold the backer once removed.

A home-made device for earring removal is described on the Instructables.com web site (http://www.instructables.com/id/Earring-removal/). This device is made from a bolt, a common wing nut, and two common staples. A hole is drilled through each flange of the wing nut. One staple is attached through each hole to make hooks that slip into the loops of a butterfly backer. A bolt is then threaded into the wing nut. As the bolt is threaded through the wing nut, the end of the bolt presses against the tip of the post and pushes the post back down through the backer, which is being held in place by the hooks (staples) connected to the wing nut. The drawbacks to this device are numerous. The device is aesthetically not appealing. The components are made of industrial hardware, they are relatively heavy, and have sharp edges. The device is large, which makes it difficult to access the space behind the ear. The device requires two hands to be used in close proximity to the earlobe and earring. The device requires two hands to provide a turning motion of the bolt relative to the wing nut. If the user does not carefully control this turning motion, the user will twist the earlobe, which could cause pain and soreness. If the user stops turning the bolt, the device does not necessarily disengage from the earring. This device therefore does not either provide an easy or a safe way to remove an earring.

Therefore, in light of these prior art examples, an aesthetically appealing and simple device is needed that allows easy interfacing with an earring and controlled removal of an earring with only one hand.

SUMMARY

The present invention provides devices and related methods that can be used to remove earrings of the type in which an earring with a post is held in position by a backer that engages the post such as by friction or via a snap fit engagement or otherwise. Described briefly, the devices include features such as tips that easily interface with the earring and backer to facilitate removal. The tips are coupled to a structure with a spring characteristic. Simple squeezing of the structure actuates the tips to separate the backer from the post. The spring characteristic is biased to keep the tips spaced apart, or open, in the absence of a squeezing force. The present invention offers numerous advantages over other removal devices.

The principles of the present invention can be incorporated into devices that are simple and easy to manufacture. The devices can be fabricated using a wide range of economical, practical manufacturing techniques including injection molding, thermoforming, stamping, 3d-printing, casting, machining, and the like.

Preferred embodiments can be fabricated as single, integral pieces to simplify manufacture and promote low cost design. The devices can be fabricated from a wide range of materials including thermoplastic and/or thermosetting polymers, ceramic materials, metallic materials, wood or other cellulosic material (natural or synthetic), combinations of these, and the like. Clear or transparent material is preferred for the removal device to allow a user to view the earring through the device during removal. The devices can be made to be aesthetically appealing with different styles, colors, etc. In preferred embodiments, the devices are lightweight.

The principles of the present invention allow safe, soft and gentle removal of a wide variety of earrings, including those held in place by butterfly-style backers.

The devices can maintain their grip on the backer after the backer is removed from the stud to avoid dropping or otherwise losing the backer after the earring is separated and the backer removed.

In many embodiments, the devices allow single-handed separation of the earring components once the device is engaged with the earring. The devices can be operated with two fingers of one hand to separate the two components of a stud earring without applying a load (force) on the ear. The devices remove the earring in a controlled fashion in that the relative motion of the tips is controlled. In many embodiments, the device pushes the post out of the backer completely or almost completely.

Illustrative embodiments of the removal devices are easy and comfortable to use, since the actuation portion readily fits into the hand of a user and then decreases in size to the tips that insert into the earring. Actuation occurs in many embodiments via a natural squeezing motion of the device. The squeezing motion is more controllable and ergonomic when compared to separating motions of the hand and fingers. Devices incorporating the principles of the present invention are very simple to use, even for children. The device allows fast, simple, and safe backer removal. The devices are versatile. For example, a single device configuration can work with a variety of earring and backer sizes.

The devices incorporate a spring feature that helps to keep the tips that engage the earring biased open. This is an advantage because it makes it easier for the user to engage and disengage the tips with the earring.

In one aspect, the present invention relates to a device for removing an earring held in position at least in part by a backer engaging a post of the earring. The device comprises: a first tip having a surface and optionally comprising a projection extending from the first tip; and a second tip comprising at least one feature that engages the backer mounted on the post; and a structure that couples the first tip to the second tip, said structure comprising a spring characteristic; wherein (i) the spring characteristic is biased to cause the first and second tips to be separated from each other in a neutral position corresponding to an absence of a squeezing force applied to the coupling structure; (ii) the first tip is able to engage the post during at least a portion of the time that the second tip engages the backer; and (iii) the structure is coupled to the tips in a manner such that applying a squeezing force to the structure causes the tips to move towards each other such that one or both of the surface of the first tip and the optional projection extending from surface of the first tip engages and applies a force against the post of the earring and the second tip engages and applies a force to the backer to help remove the backer from the post.

In another aspect, the present invention relates to a device for removing an earring held in position at least in part by a backer engaging a post of the earring, said device comprising: a first tip having a surface and optionally comprising a projection extending from the surface of the first tip, said optional projection being sized to fit between first and second features of the backer in a manner effective to engage the post of the earring during at least a portion of the time that the device is used to help remove the backer from the post; a second tip comprising at least one projection that fits against a feature of the backer in a manner effective to engage the backer during at least a portion of the time that the device is used to help remove the backer from the post; an arcuate structure coupling the first and second tips and having a spring characteristic such that applying a squeezing force to the structure causes the first and second tips to move towards each other, said spring characteristic being biased such that the first and second tips are spaced apart in a neutral position in the absence of the squeezing force; and a first alignment feature associated with the first tip and a second alignment feature associated with the second tip, said alignment features cooperating to help the first and second tips move toward each other in a desired alignment during at least a portion of the time that the squeezing force is applied to the arcuate structure.

In another aspect, the present invention relates to a method of removing an earring held in position at least in part by a backer engaging a post of the earring, the method including the steps of: providing a device as described herein; causing the first tip to engage the post of the earring; causing the second tip to engage the backer; and applying a squeezing force to the device in a manner such that movement of the tips helps to remove the backer from the post. In a similar aspect, the method includes a step of applying a squeezing or compression force to the device to move the tips toward one another to help to remove the backer from the post.

In preferred aspects of such methods, a unique earring removal device is provided that includes at least one arm structure connecting the tips for interfacing with earring components. The arm structure allows the tips to move relative to one another when a compression force is applied to the structure, yet keeps the tips naturally separated when no force is applied to the arm structure by the user.

In one preferred arrangement, the arm structure is a single piece having two continuous and integral arms, e.g., one arm loops around and connects seamlessly to another arm to make a generally "U" shaped structure. The arms connected together in this fashion inherently act as springs when made from suitable material(s). The tip of one arm has features such as tines or prongs to interface with a butterfly type backer. The tip of the other arm has features such as a flat contact surface, optionally with one or more projecting ribs suitably positioned to push the stud or post of the ornamental component out from the backer. If present, the one or more rib(s) used for pushing against the post are oriented on, the contact surface to fit between the butterfly loops and engage the stud post.

In an alternative embodiment of the invention, first and second arms pivotably connect at a hinge-type pivot point allowing the arms to move in a manner similar to a scissor action. A leaf spring, compression spring, torsion spring, or the like biases the arms of the device so that the tips are biased open in a neutral position. Actuating the arms causes the tips to close. The spring(s) may also be integral with one or both arms.

In a further alternative embodiment, a device has tips that are coupled through a set of linkages and hinges to lever arms that the user can squeeze to cause the compressive motion of the tips towards each other. As before, a leaf, compression, torsion or other type of spring biases the tips of the device open or spaced apart from each other. Actuation of the arms closes the tips, or brings them toward each other.

While multiple embodiments are disclosed, still other embodiments of the present invention will become apparent to those skilled in the art from the following detailed description, which shows and describes illustrative embodiments of the invention.

Accordingly, the drawings and detailed description are to be regarded as illustrative in nature and not restrictive.

BRIEF DESCRIPTION OF THE DRAWING

The accompanying drawings, which are incorporated in and constitute a part of this disclosure, illustrate several aspects of the present invention and together with description of the exemplary embodiments serve to explain the principles of the invention. Additionally, foregoing and other objects, features and advantages of the invention will be apparent from the following description of preferred embodiments of the invention, as illustrated in the accompanying drawings in which like reference characters refer to the same parts throughout the different views. The drawings are not necessarily to scale, emphasis instead being placed upon illustrating the principles of the invention. A brief description of the drawings is as follows.

DETAILED DESCRIPTION OF THE INVENTION

Exemplary embodiments of the present invention are described below with reference to the drawings, it should be understood that such embodiments are by way of example only and merely illustrative of the many possible embodiments which can represent applications of the principles of the present invention. Various changes and modifications obvious to one skilled in the art to which the present invention pertains are deemed to be within the spirit, scope and contemplation of the present invention as further defined in the appended claims. The exemplary embodiments of the present invention described herein are not intended to be exhaustive or to limit the present invention to the precise forms disclosed in the following detailed description. Rather the exemplary embodiments described herein are chosen and described so those skilled in the art can appreciate and understand the principles and practices of the present invention.

Figure 1:
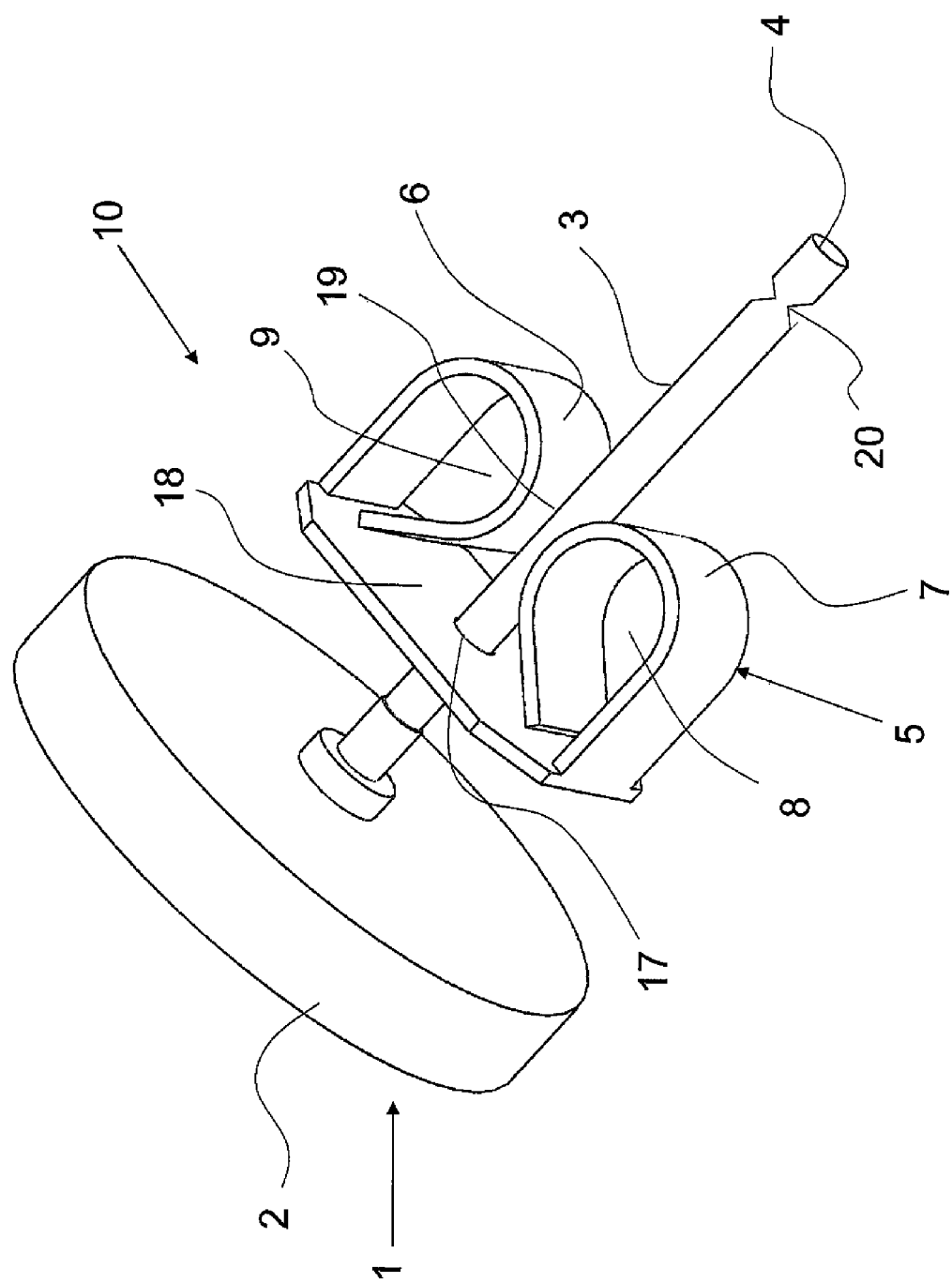
FIG. 1 is a perspective view of a generic stud earring showing a backer and an ornamental component including a post mounted to and projecting from an ornamental piece.

Referring to FIG. 1, a typical stud earring 10 is shown and includes two components. The first component is an ornamental component 1 that has an ornamental piece 2 connected to a post 3 (also referred to as stud or shaft) that has a distal tip 4. This tip 4 is shown in FIG. 1 as flat at the end, but can be rounded or even pointed, as in the case of a starter earring. The second component of stud earring 10 is a backer 5 that has two loops 6, 7 extending from a base 18 and a hole or aperture 17 therebetween through base 18. Each loop 6, 7 defines a central, inside area 8, 9, respectively. Backer 5 of FIG. 1 is commonly referred to as a "butterfly" backer; other backers that interface with the post of a stud earring exist and are described below. When backer 5 is attached to ornamental component 2, loops 6, 7 have a spring force that is biased inward to press against and grip post 3 with a friction grip as shown in FIG. 1 at location 19. In some embodiments post 3 has a partial or concentric groove 20 that makes it more difficult for backer 5 to slip off. This latching feature is common with starter earrings.

Figure 2:
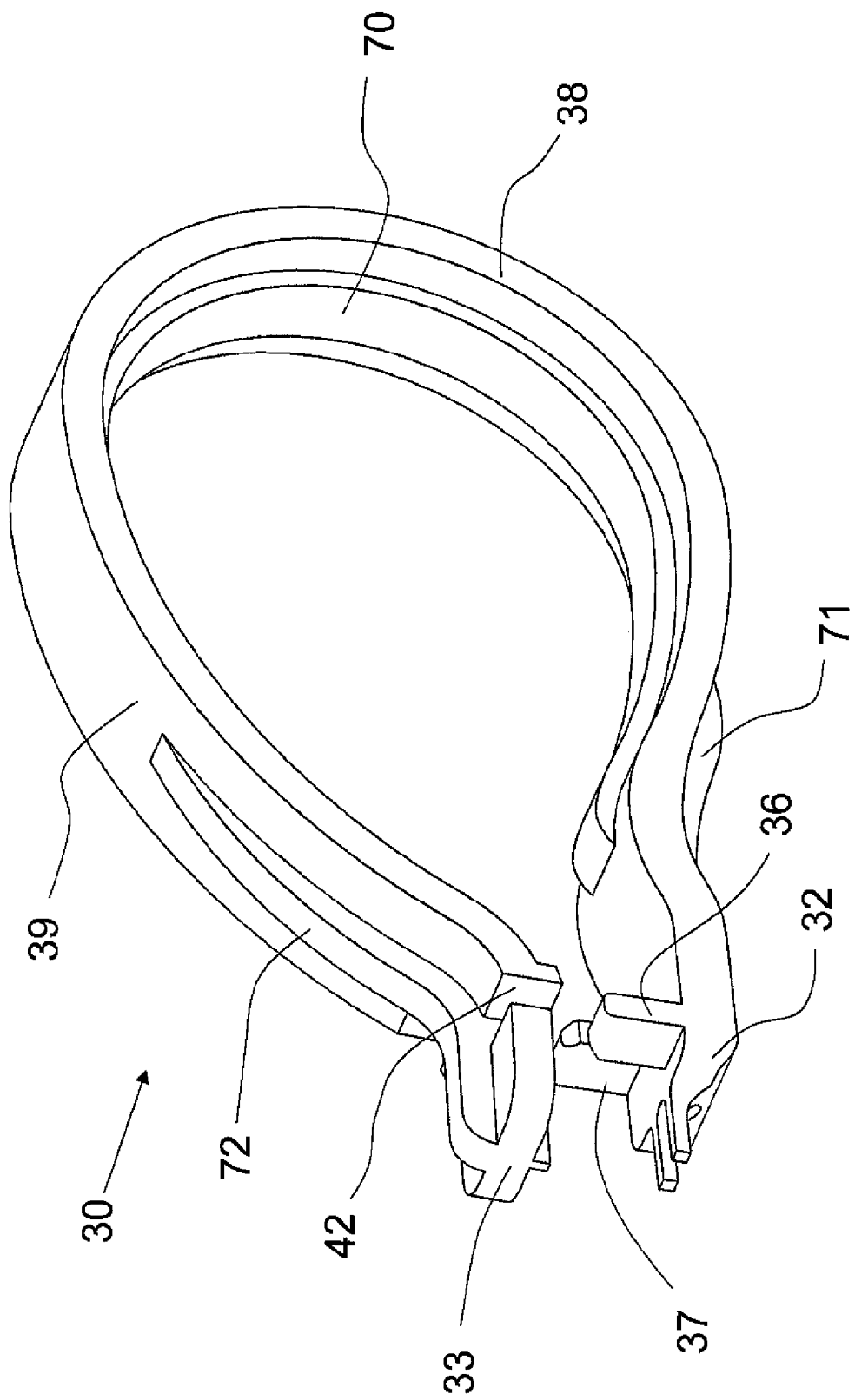
FIG. 2 is a perspective view of a preferred embodiment of an earring removal device of the invention.
Figure 3:
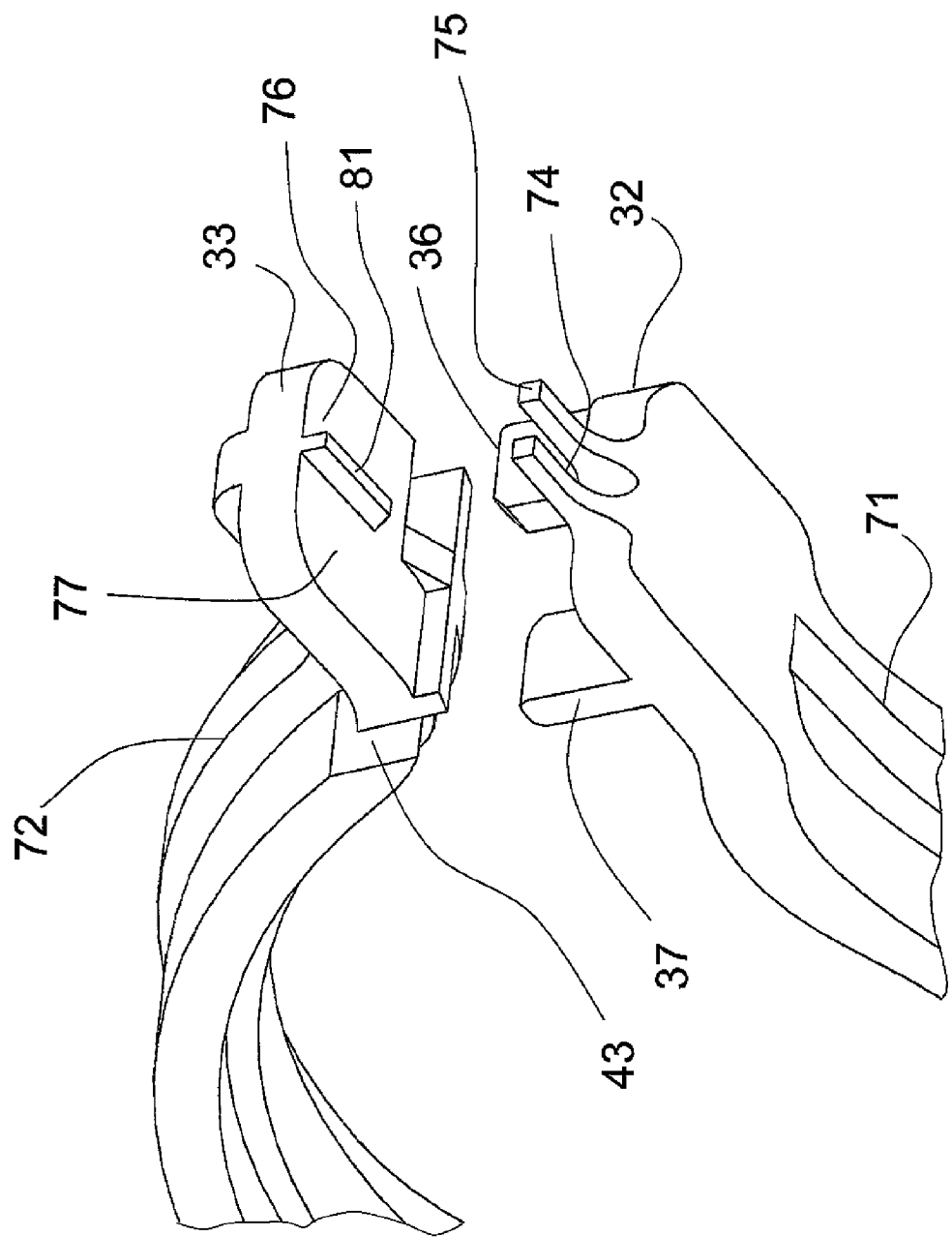
FIG. 3 is a perspective view of the tips of the preferred embodiment in FIG. 2.

FIGS. 2 and 3 illustrate a preferred embodiment of an earring removal device 30 of the present invention having tips 32, 33. Tips 32, 33 are connected to actuation arms 38, 39 respectively, which in this preferred embodiment are connected together so as to be one, arcuate, seamless piece interconnecting tips 32, 33. Arms 38, 39 incorporate a spring characteristic so that the arms are biased in a manner that helps to maintain tips 32, 33 in a spaced apart position as shown in FIGS. 2 and 3. Squeezing arms 38, 39 compresses the arms, moving them together, which in turn, causes tips 32, 33 to move towards each other. When the squeezing force is removed, arms 38, 39, and consequently tips 32, 33, spring open. In this way, a person can use one hand, such as via their fingers, to apply a squeezing motion to anus 38, 39 causing them to move towards each other. The squeezing force can additionally or alternatively be applied directly to tips 32, 33. Tips 32, 33 interface directly with a stud earring such as earring 10 in FIG. 1.

The stiffness, and hence spring force, of arms 38, 39 can be adjusted by changing one or more of the material and/or cross sectional shape of one or both arms 38, 39, or the juncture between the arms. One manner in which to accomplish this involves adding stiffening features, such as ribs 70, 71 and 72.

In order to maintain tips 32, 33 properly aligned relative to one another, device 30 may include one or more alignment features. For example as illustrated, tips 32, 33 may include alignment features such as posts 36, 37 on tip 32 that interface with corresponding slots 42, 43 on tip 33. The latter slot 43 is best seen in FIG. 3. These and other alignment features may be located at or proximate the area where tips 32, 33 connect to or transition to arms 38, 39. The arrangement of alignment features can be swapped. For instance, posts can be on tip 33 and slots on tip 32. Alternatively, a slot and post can be provided on tip 32 while a corresponding post and slot are on tip 33. Lesser or greater numbers of corresponding alignment features can be used if desired.

Figure 5:
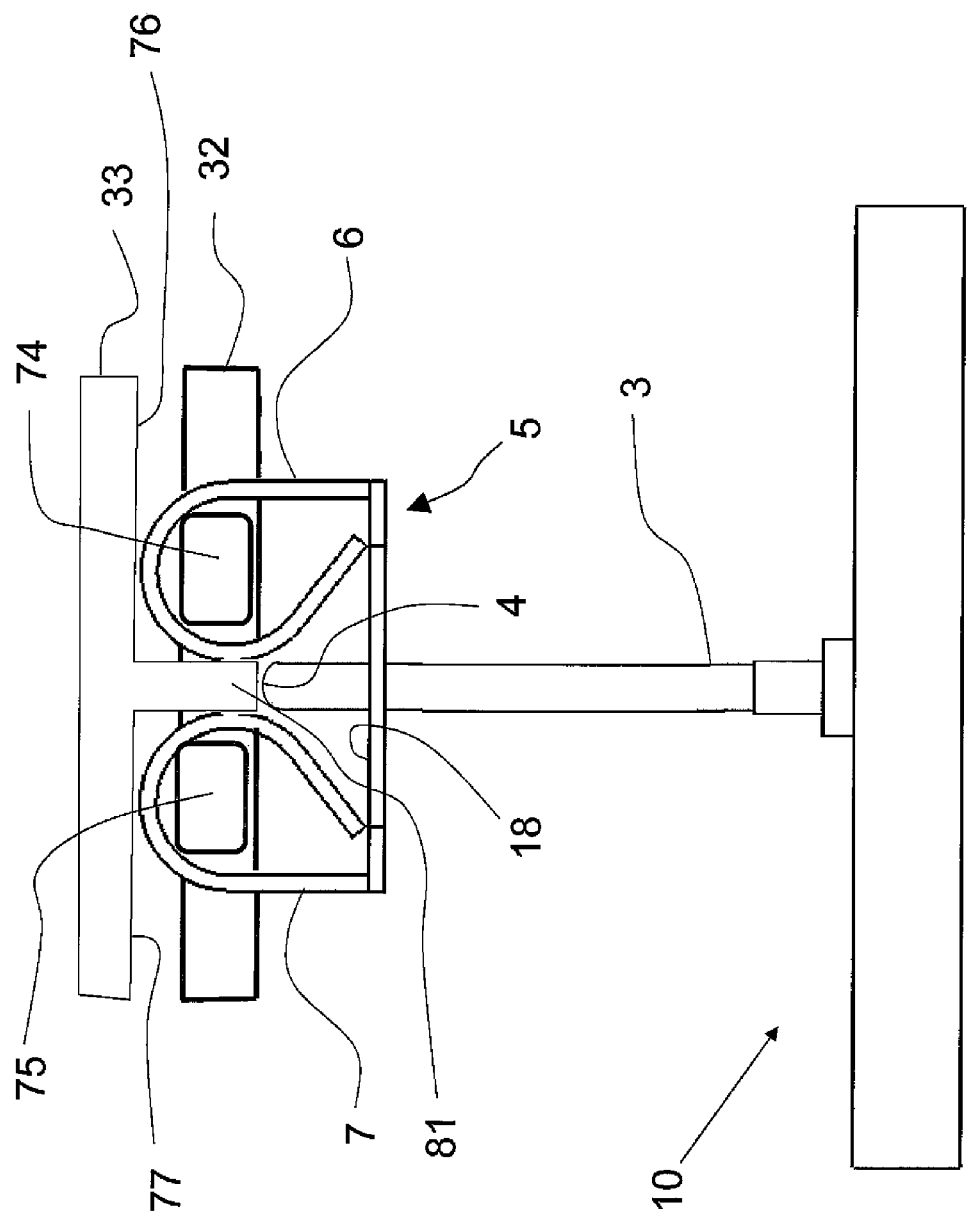
FIG. 5 is an end view of the preferred embodiment of FIG. 2 engaged with the earring of FIG. 1, with the tips fully closed.

Referring now to FIG. 3, the details of tips 32, 33 and the features that facilitate interaction with earring 10 (FIG. 1) are described. FIG. 3 shows a close up of tips 32, 33. Tip 32 has two, projecting tines or prongs 74, 75 that extend from tip 32 in a manner effective to fit through and engage with earring backer 5, particularly inside areas 8, 9 of earring backer 5. Prongs 74, 75 can be blades that can additionally or alternately be slipped between backer 5 and the earlobe or other body part if sufficient space exists between the body part and backer 5 to allow this. The other tip 33 has face defined by surfaces 76, 77 (e.g., flat surfaces) with a rib 81 that projects out between surfaces 76, 77. When engaging earring components during a removal operation, projecting rib 81 presses against and engages tip 4 of post 3 of earring 10. The size and shape of rib 81 can be of different sizes and, as shown more clearly in FIG. 5, is preferably rectangular in shape and is about the same width as earring post 3, so that rib 81 can push against and apply a force to tip 4 of post 3. Surfaces 76, 77 provide support for rib 81 and also provide back up functionality in case tip 4 slips off rib 81 during actuation. If such slippage happens, surfaces 76, 77 can contact and continue to press post 3 through backer 5 until at least one of surface(s) 76 and/or 77 contacts backer loops 6, 7.

Squeezing arms 38, 39 causes relative motion therebetween so that tips 32, 33 move toward each other. As tips 32, 33 move toward each other, rib 81 pushes in one direction against post 3, while prongs 74, 75 engaged with backer 5 to cause relative movement of backer 5 in the other direction. Actuation may continue until post 3 is pressed far enough through backer loops 6, 7 such that post 3 separates or is easily separated from aperture 17 and backer 5. The user can then release actuation arms 38, 39, which causes arms 38, 39, and hence tips 32, 33, to spring open. In some embodiments, prongs 74, 75 maintain engagement with the removed backer 5, allowing easy collection for subsequent handling or storage.

Figure 4:
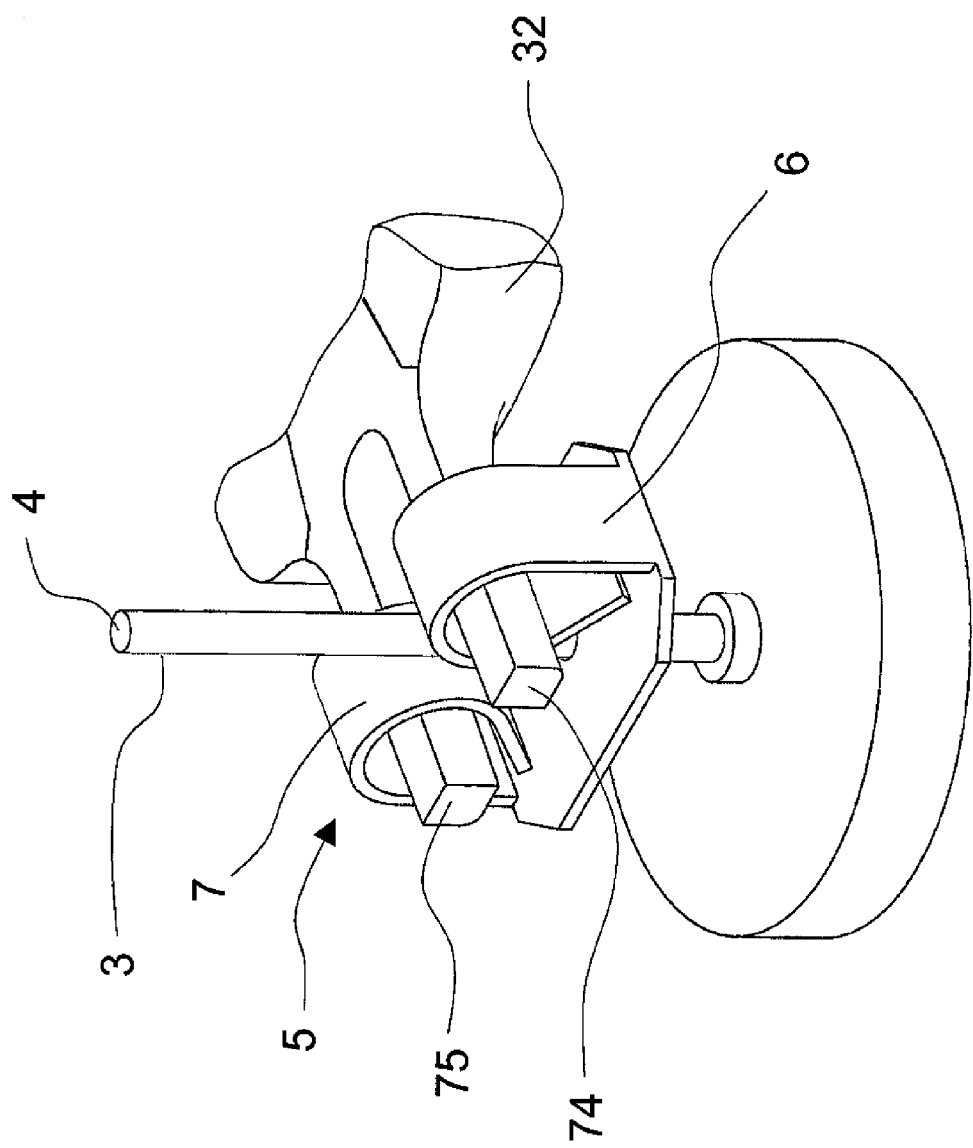
FIG. 4 is a perspective view of one of the tips of the preferred embodiment in FIG. 2 engaged with the backer of the earring of FIG. 1.

Referring now to FIG. 4, tip 32 of removal device 30 is shown interfaced with backer 5 of the earring of FIG. 1. This figure shows how the two prongs 74, 75 of tip 32 fit into openings 8, 9 (FIG. 1) of backer loops 6, 7. When engaged in this manner, actuation arms 38, 39 can be squeezed together so that tip 33 (not shown in FIG. 4) engages tip 4 of post 3 while prongs 74, 75 engage backer loops 6, 7.

FIG. 5 shows a simplified end view of the removal device engaged with earring 10; in this figure, tips 32, 33 are fully closed. This fully closed position occurs when prongs 74, 75 are within loops 6, 7 and surfaces 76, 77 of tip 33 are in contact with the tops of backer loops 6, 7. In other embodiments, the fully closed position may be controlled by other feature engagement. For example, other embodiments may have a deeper rib 81 so that the fully closed position occurs when rib 81 contacts base 18 of backer 5.

As seen in FIG. 5, rib 81 has pressed post 3 sufficiently far down relative to backer 5 so that the ornamental component and post 3 can be separated from backer 5 with ease. In this embodiment, tip 4 of post 3 is shown pushed past the area of loops 6, 7 that contact the post 3 for easy removal (that is, loops 6, 7 no longer contact post 3). However tip 4 does not have to be fully moved past loops 6, 7 to allow easy removal. For instance, in the case of a post 3 with a groove (not shown in FIG. 5, but shown in FIG. 1), it may be sufficient to disengage the contact areas of loops 6, 7 away from groove 20 to release the locking action. If the user continues to keep arms 38, 39 of the device squeezed after removal, so that tips 32, 33 remain in contact with backer 5, then the device's grip on backer 5 is maintained. Backer 5 can be lifted away from the ear, keeping this very small piece from dropping and being lost.

Figure 6:
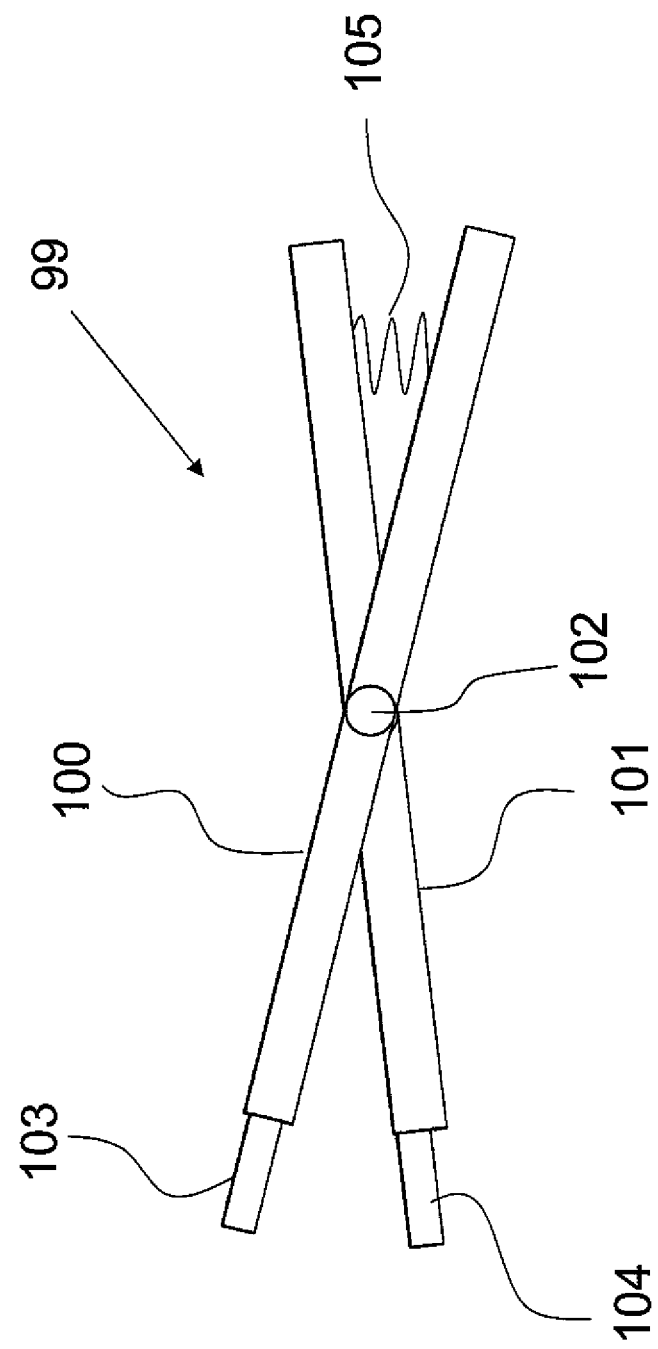
FIG. 6 is a side view of an alternative embodiment of a device of the present invention including arms that are pivotably coupled by a pivot hinge.

An alternative embodiment of an earring removal device 99 of the present invention is schematically shown in FIG. 6. Device 99 has actuation arms 100, 101 that are pivotably connected at a hinge point 102 instead of having a seamless connection. To bias tips 103, 104 of arms 100, 101 open, a spring 105 is placed between actuation arms 100, 101, with hinge point 102 positioned between tips 103, 104 and spring 105. Spring 105 is depicted as a compression coil spring, but can be of many other types, such as a leaf spring or a torsion spring. Spring 105 is shown placed at the rear of device 99, distal from hinge point 102 and even more distal from tips 103, 104, however, spring 105 can alternately be positioned at any optimal place along arms 100, 101 including at or more locations proximal to hinge point 102.

Figure 7:
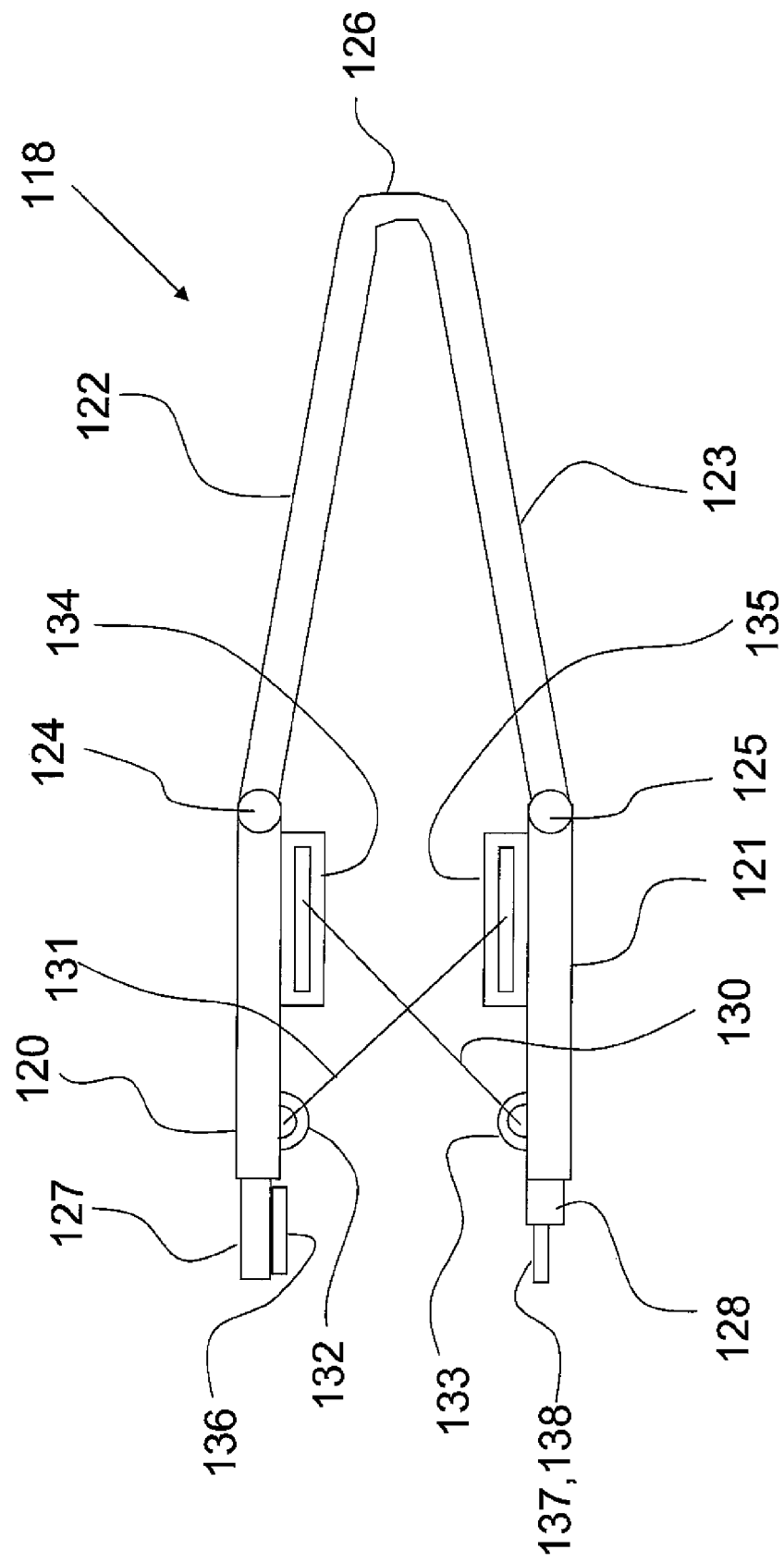
FIG. 7 is a side view of an alternative embodiment of a device of the present invention with arms that are coupled by multiple pivot hinges to allow more aligned motion of the tips relative to each other.

Another embodiment of a device according to the invention is device 118 in FIG. 7, which includes multiple arms pivotally connected at multiple locations. Primary actuation arms 120, 121 are connected to a second set of actuation arms 122, 123 at hinges 124 and 125 respectively. These second actuation arms 122, 123 are seamlessly connected together at a back end 126. The seamless connection provides an inherent shape and spring-return force that keeps tips 127, 128 of primary arms 120, 121 naturally open. The second set of actuation arms 122, 123 allows primary arms 120, 121 and the associated rib 136 and prongs 137, 138 to remain parallel to one another during actuation as the arms are squeezed and tips 127, 128 are brought together. A set of guides 130, 131 provides a mechanism to keep arms 120, 121 parallel during actuation. One end of each guide 130, 131 pivots at hinge locations 132, 133, respectively, as the other ends slide in slots 134, 135. If back end 126 is replaced with a hinge, for instance, then a separate spring, such as a compression coil spring, can be inserted between primary arms 120, 121 or between secondary arms 122, 123. This would function in a manner similar to mechanical spring 105 depicted in FIG. 6. Alternatively, the end of guides 130, 131 could be rigidly fixed at locations 132, 133 rather than be free to pivot. This would cause guides 130, 131 to function as springs that help to keep arms 120, 121 biased open when no squeeze or closing action is applied to device 118.

Figure 8:
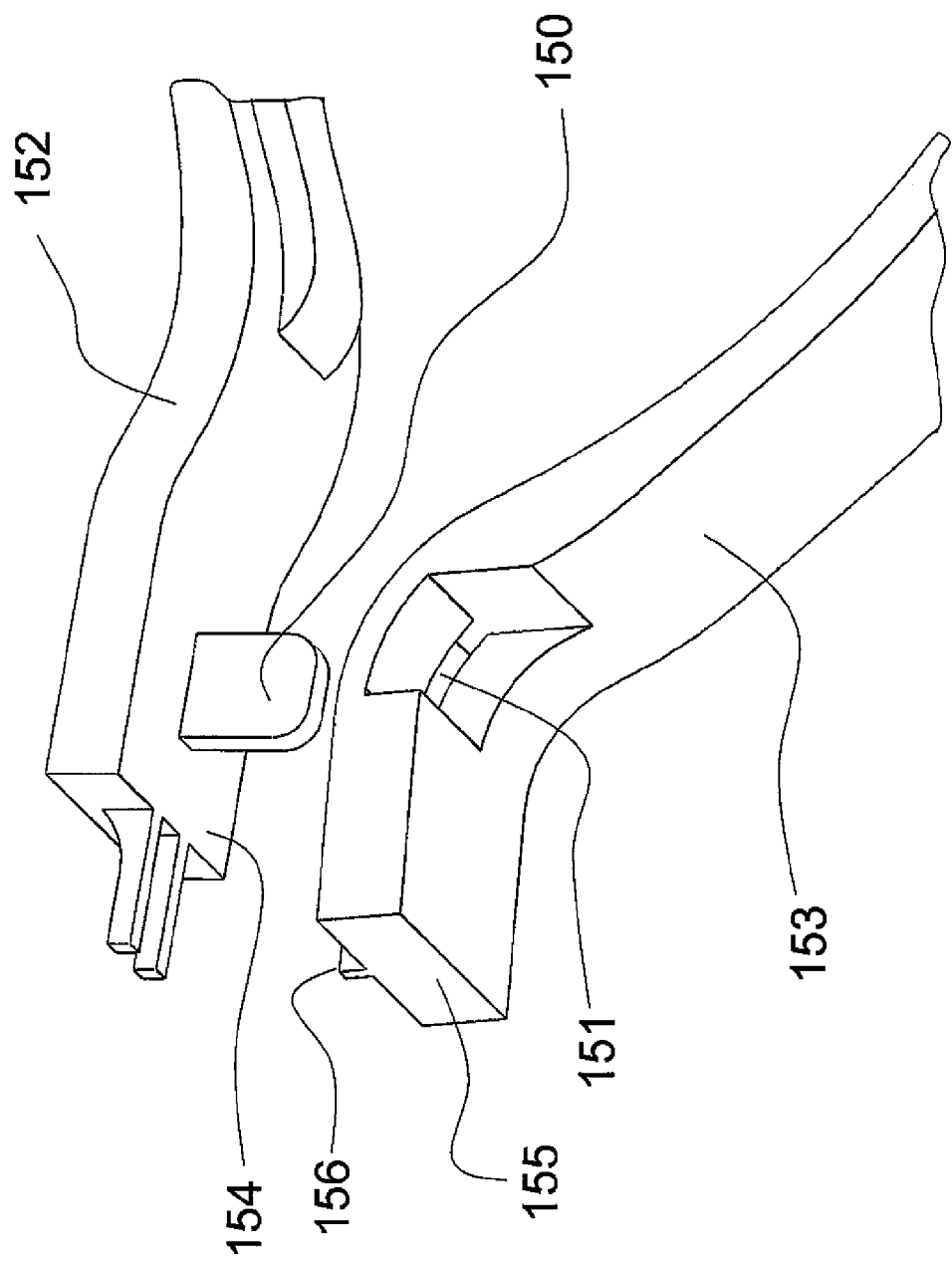
FIG. 8 is a perspective view of an alternative embodiment of a device of the present invention having an alignment feature.

Various alignment features may be used to maintain the alignment of the two tips of the removal device. FIGS. 2 and 3 illustrated alignment features posts 36, 37 on tip 32 that interface with corresponding slots 42, 43 on tip 33. Alternate alignment features may be used. FIG. 8 illustrates one example of a different alignment feature that can be incorporated into a removal device similar to device 30 of FIGS. 2 and 3. The embodiment of FIG. 8 shows a single post 150 on tip 154 attached to arm 152 and a slot 151 through tip 155 attached to arm 153. Post 150 slips through slot 151 when arms 152, 153 are squeezed together. The cooperating alignment features 150, 151 desirably should be as close to tips 154, 155 as possible to help ensure good alignment between rib 156 on tip 155 and the post of an earring when the removal device is engaged with the earring.

Figure 9:
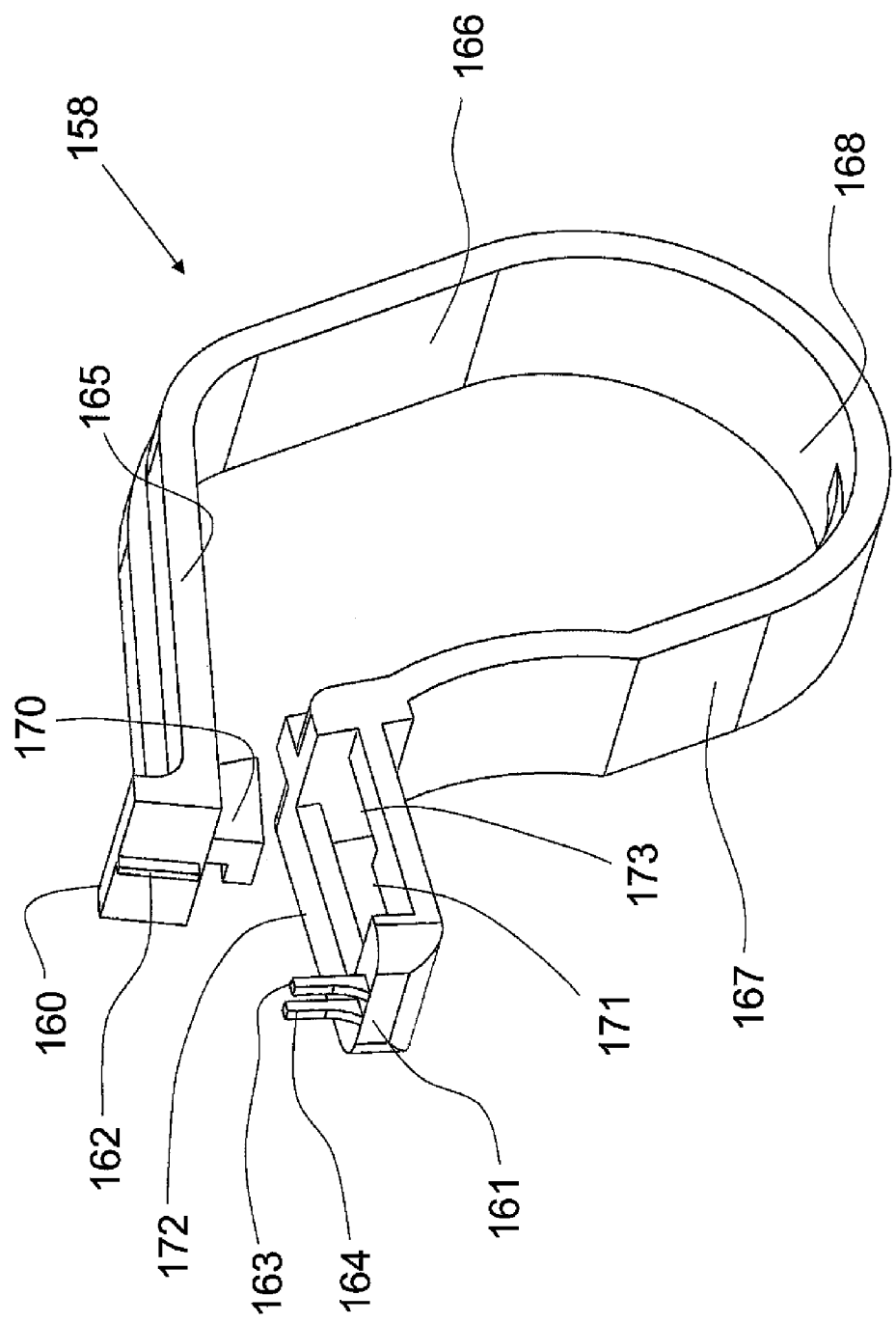
FIG. 9 is a perspective view of an alternative embodiment of a device of the present invention that provides parallel motion of a rib of a first tip to the prongs of a second tip.
Figure 10:
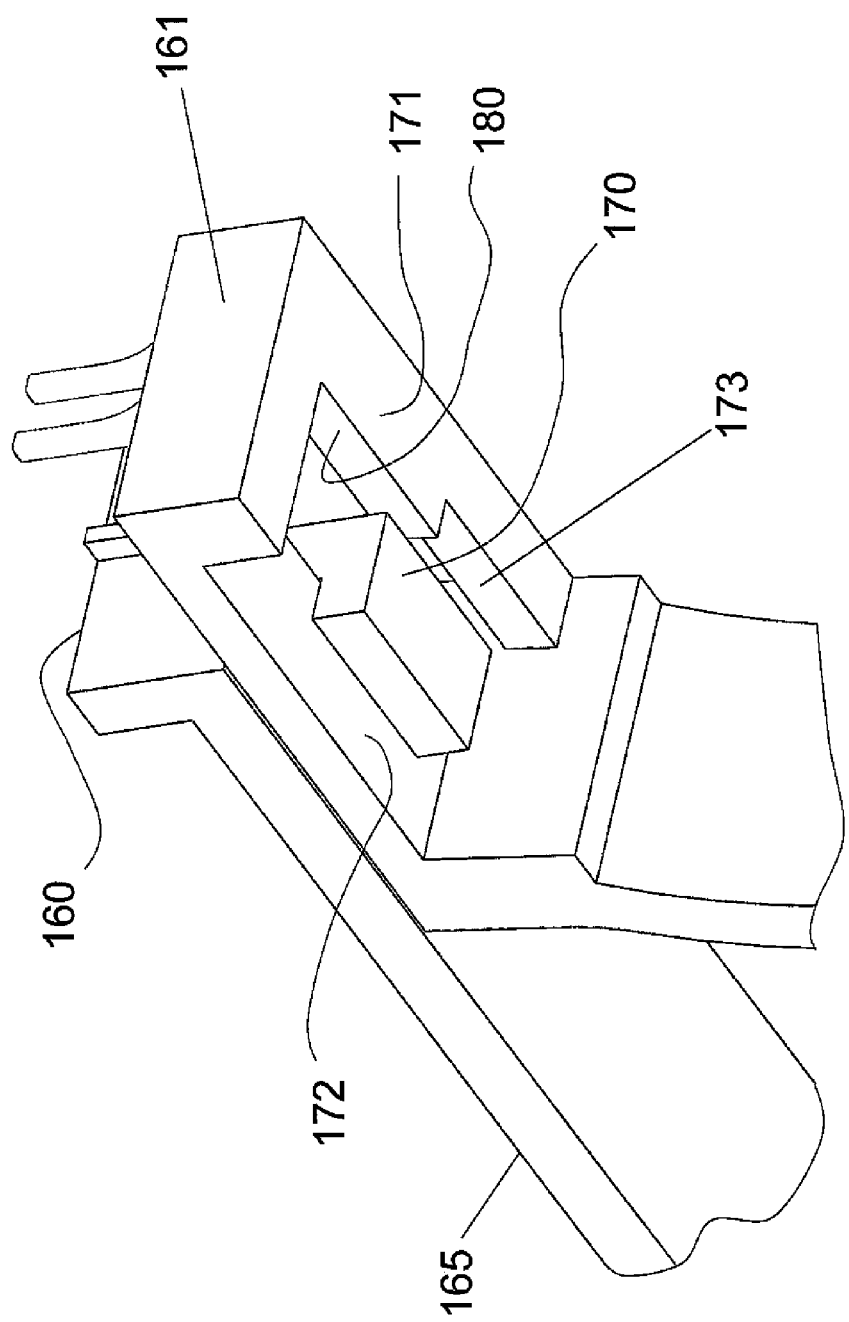
FIG. 10 is an alternate perspective view of the alternative embodiment of FIG. 9 in an assembled state where a guide boss of a first tip is engaged with guide tracks of the second tip.

Variations of the way in which the rib of the first tip and the prongs of the second tip can be made to move relative to each other in a manner effective to facilitate earring removal are also possible. Desirably, such movement is co-linear and may be parallel or along the same axis in any plane. An embodiment of a removal device 158 that can be made as a single molded, component, for example, is shown in FIGS. 9 and 10. FIG. 9 shows device 158 in a configuration as it would be as fabricated or molded, with no squeezing force acting thereon. Device 158 has tips 160, 161, with tip 160 connected to actuation arm 166 by an extension arm 165, and tip 161 connected to actuation arm 167. The two actuation arms 166, 167 are connected together seamlessly at region 168 in a manner effective to provide the inherent spring force to keep tips 160, 161 naturally open in the absence of a squeezing force. Earring remover 158 again has the two tips where first tip 160 has rib 162, and second tip 161 has two prongs 163, 164. Device 158 also includes alignment features; tip 160 includes a guide boss 170 and tip 161 includes tracks 171, 172.

FIG. 10 shows device 158 with guide boss 170 positioned between guide tracks 171, 172 so that extension arm 165 is oriented largely parallel to tracks 171, 172, and device 158 is ready to be used for removing an earring. A user can then squeeze arms 166, 167 together with an actuation force, which causes tips 160, 161 to be brought together. Tips 160, 161 move laterally toward each other when the structure coupling the tips (i.e., region 168) is squeezed. On tip 160, rib 162 and the planar faces on either side of rib 162 are at an orthogonal angle relative to extension arm 165, and prongs 163, 164 of tip 161 are also at an orthogonal angle relative to track 171, 172. During actuation, prongs 163, 164 moved parallel to rib 162. The angle of tip 160 with rib 162 and angle of prongs 163, 164 relative to extension arm 165 and tracks 171, 172 can be obtuse, but an orthogonal angle makes it easier to remove the earring and hold the backer afterward removal.

To operate device 158, guide boss 170 is first slipped underneath and engaged into guide track 172, as illustrated in FIG. 10; track 172 may include a larger opening at section 173 to facilitate engagement of boss 170 under track 172. This brings tips 160, 161 in close proximity to and optionally touching each other. The side face 180 of track 171 helps keep the guide boss 170 aligned during the actuation motion.

Figure 11:
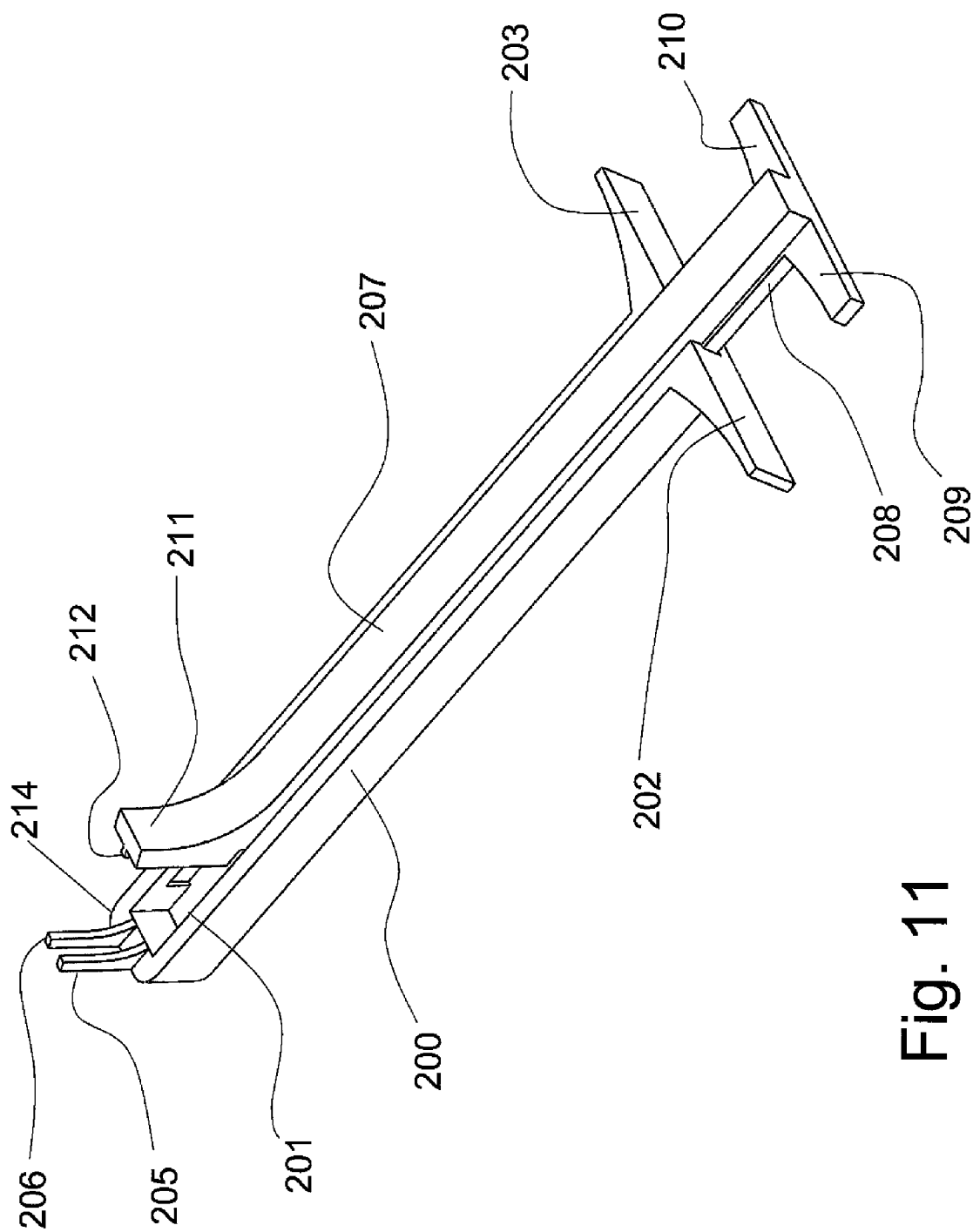
FIG. 11 is a perspective view of a two-piece alternative embodiment of a device of the present invention where the two separate pieces slide relative to each other.

Yet another embodiment that provides parallel motion of the rib to the prongs is shown in FIG. 11. In this embodiment, the removal device has a body 200 and a pusher 207 in slidable engagement. Body 200 has track 201 extending the length thereof and distal flanges 202, 203. At the other end, body 200 has a tip 214 with prongs 205, 206. Pusher 207 engages with track 201 via a rail 208 on either side which keep pusher 207 aligned with body 200. Pusher 207 includes flanges 209, 210 at its distal end and a tip 211 with rib 212 at the other end. In use, the user can move pusher 207 forward by applying a force to flanges 209, 210 while simultaneously holding flanges 202, 203 of body 200. This motion results in pusher 207 sliding in body 200 via track 201 and rails 208, so that rib 212 moves parallel to prongs 205, 206.

Figure 12:
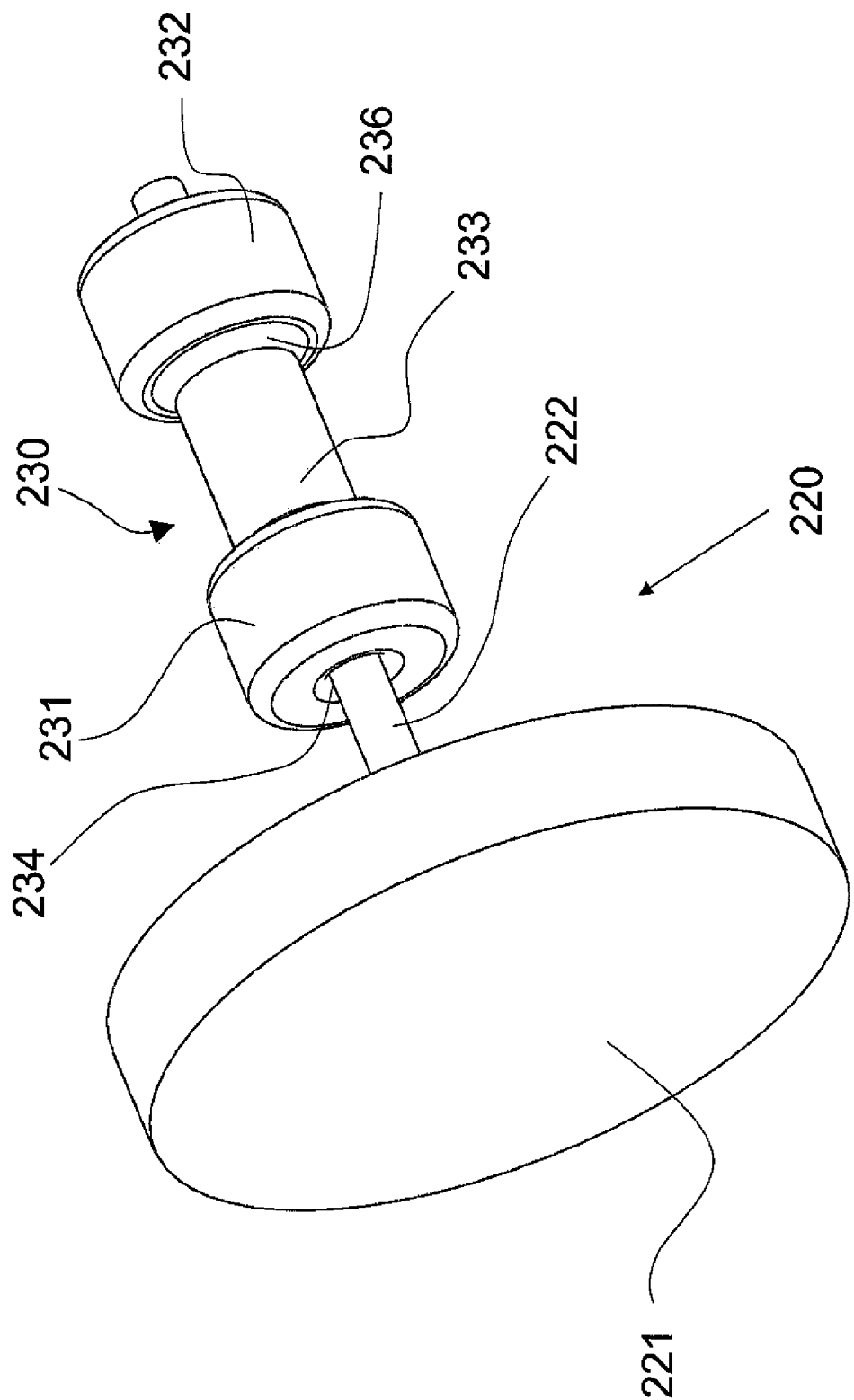
FIG. 12 is a perspective view of a generic stud earring engaged with an example of an alternative earring back.
Figure 13:
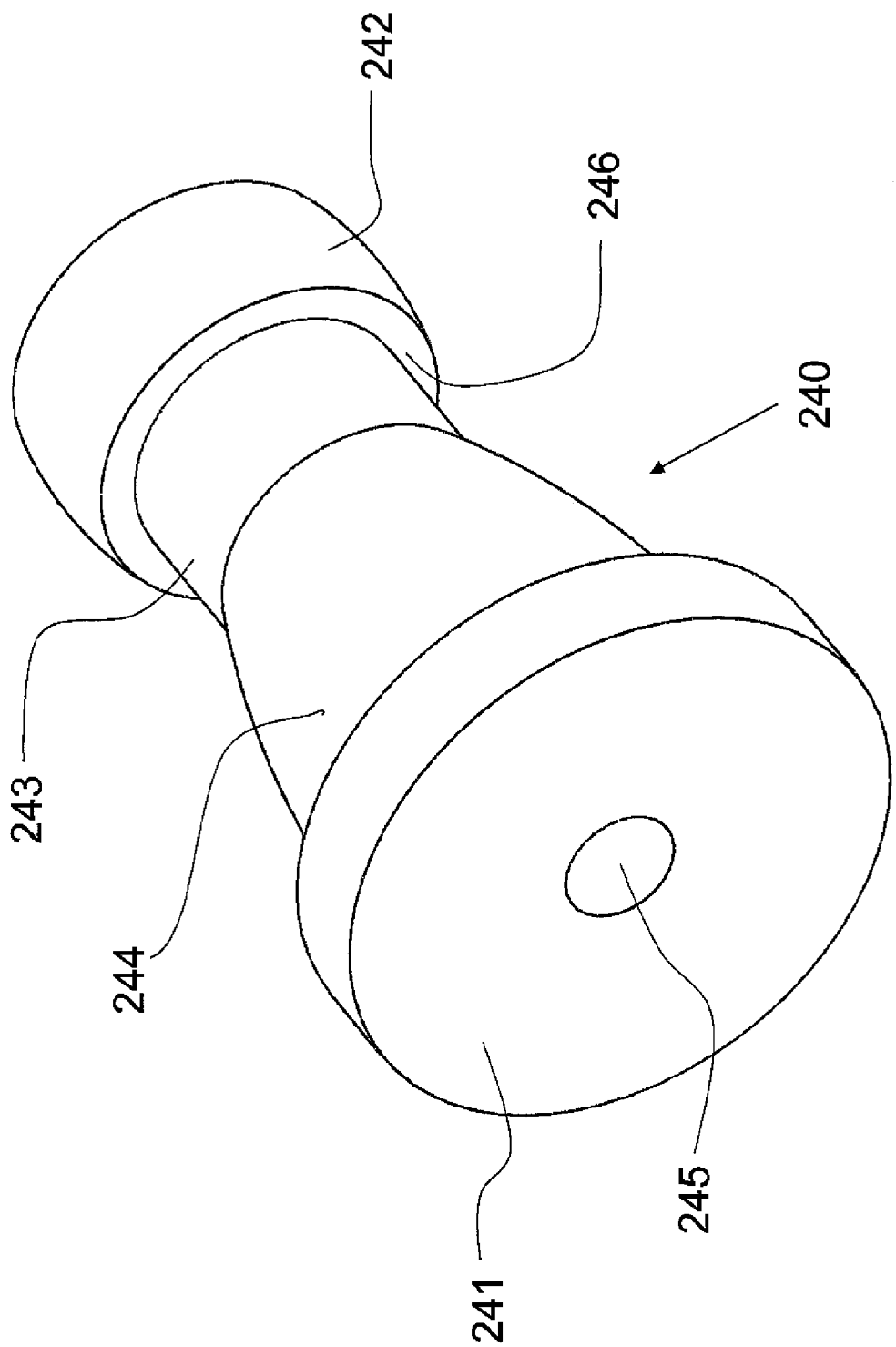
FIG. 13 is a perspective view of another alternative earring back.
Figure 14:
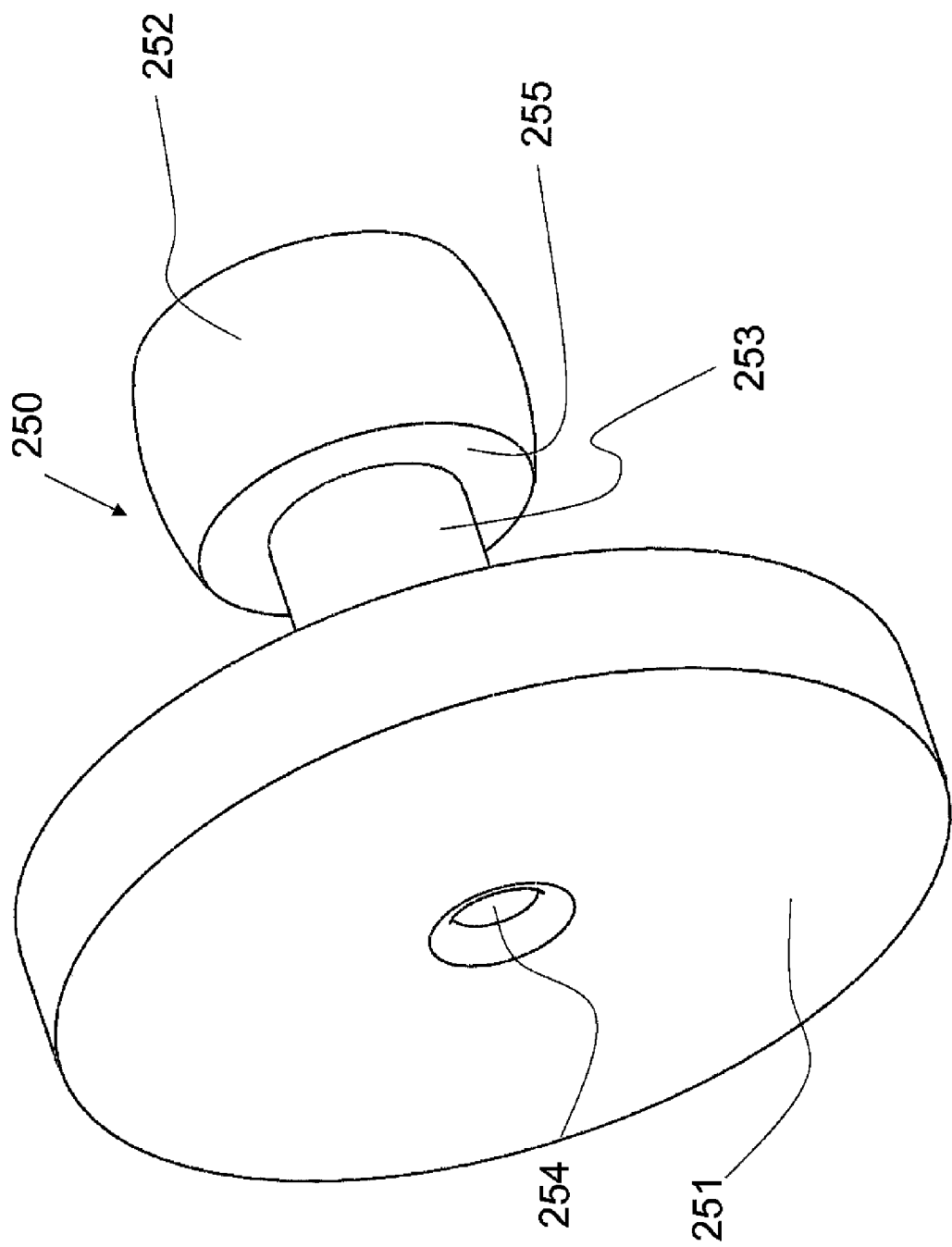
FIG. 14 is a perspective view of yet another alternative earring back.

Friction-type earring backers come in a variety of different styles, shapes, and forms. FIGS. 1, 4 and 5 illustrate a butterfly backer 5. Examples of other backers are shown in FIGS. 12, 13 and 14. These styles of backers do not have loops but rather open features against which removal devices of the present invention can interface to separate the ornamental component of an earring from the backer. FIG. 12 shows an earring 220 with ornamental component 221 and post 222 with a backer 230 positioned thereon. Backer 230 includes a hole or passage 234 through backer 230 through which post 222 of earring 220 fits to engage backer 230 on post 222. Backer 230 has a first end 231 and an opposite second end 232 that are larger in diameter or size than central section 233 that connects these two ends 231, 232. Adjacent central section 233, each end 231, 232 has a shoulder forming the transition between the different sized features. In FIG. 12, end 232 is illustrated with shoulder 236, an open feature with which removal devices of the present invention can interface.

Referring to FIG. 13, another example of a friction backer with open features is shown. This backer 240 has opposite ends 241, 242, with end 241 being larger than end 242. A center section between ends 241, 242 has a cylindrical or straight portion 243 and conical portion 244. A hole or passage 245 through backer 240 allows the post of an earring to pass through. In this embodiment, end 241 has a larger diameter than end 242 and is thereby preferred to be the end that presses against or faces towards the earlobe. With end 242 larger than section 243, a shoulder surface 246 or open feature is created with which removal devices of the present invention can interface.

Referring now to FIG. 14, yet another example of a friction backer with open features is shown. This backer 250 has opposite ends 251, 252 connected by a central cylindrical or straight section 253. A hole or passage 254 through backer 250 allows the post of an earring to pass through. End 251 is much larger in diameter than end 252 and thereby is preferred to be the end that presses against or faces towards the earlobe. With end 252 larger than central section 253, a shoulder surface 255 or open feature is created with which removal devices of the present invention can interface.

Figure 15:
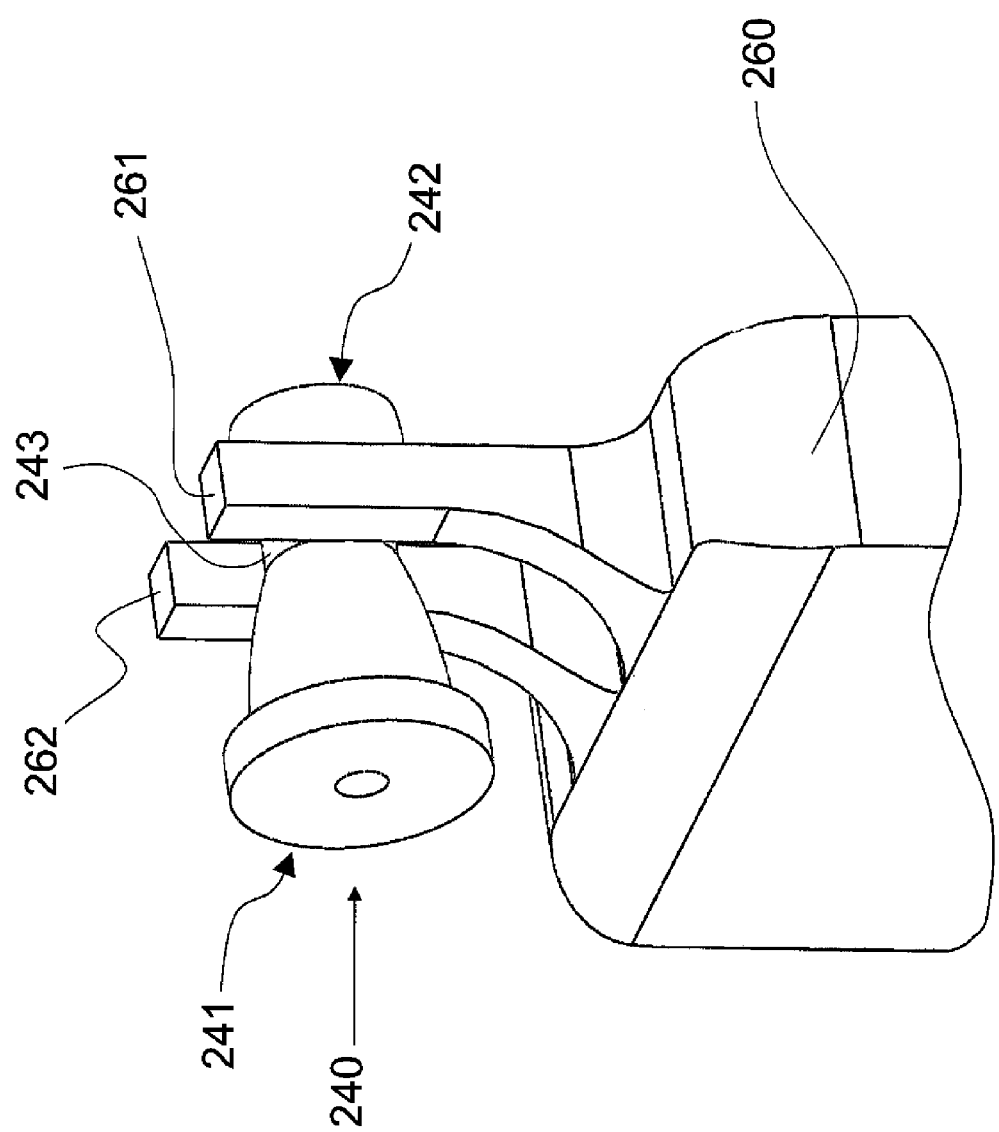
FIG. 15 is a perspective view of the alternative earring back of FIG. 13 engaged with the second tip of the preferred embodiment of FIG. 2.

In addition to removing butterfly-type backers as described above, the removal devices of this invention can be used to remove other friction backers, such as those of FIGS. 12 through 14. For example, FIG. 15 illustrates backer 240 of FIG. 13 engaged with a removal device of the invention. In FIG. 15, a tip 260, which is similar to tip 32 from the embodiment shown in FIGS. 2 and 3, is shown engaged with backer 240. Tip 260 includes prongs 261, 262 (similar to prongs 74, 75 from the embodiment shown in FIGS. 2 and 3) fit between ends 241, 242 and around central section 243 of backer 240. In use, during removal, prongs 261, 262 press against shoulder surface 246 (not seen in FIG. 15).

Figure 16:
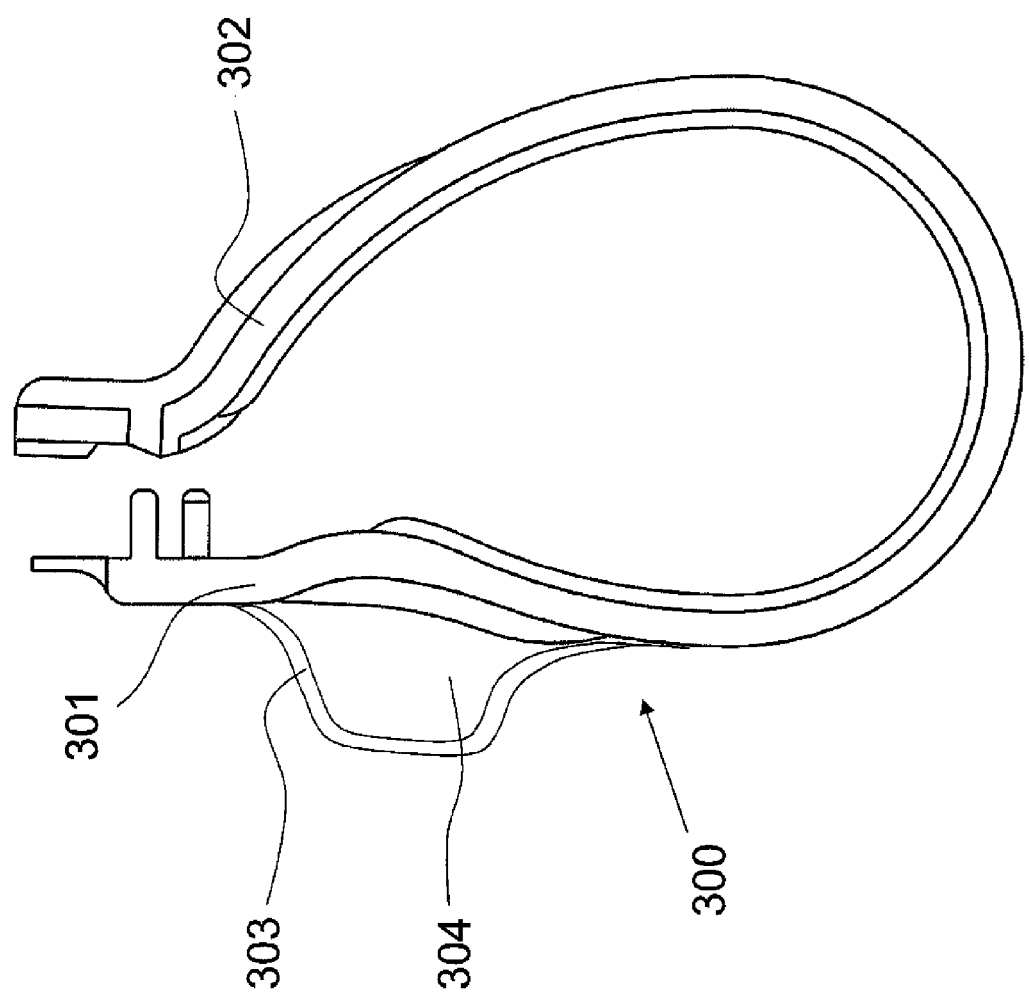
FIG. 16 is a side view of an alternative embodiment of a device of the present invention.

The removal devices of this invention can include features to make it easier for the user to hold the device, squeeze the device at the optimal place on the actuation arms, and/or to improve control of device actuation. FIG. 16 shows an embodiment in the form of device 300 with actuation arms 301, 302, each having a tip (not identified in FIG. 16). One of arms 301, 302, in this embodiment arm 301, includes a grasping feature or loop 303 that extends from arm 301 creates an opening 304. In one exemplary actuation, the thumb of a user is placed on and presses on actuation arm 302 and the index finger or other finger is placed in opening 304 and presses on actuation arm 301. Alternately, the thumb of a user can be placed in opening 304 and another finger is placed on actuation arm 302. This loop feature 303 facilitates grasping and positioning the user's hand and fingers on device 300. Loop 303 is just one example construction of a grasping feature, and other feature constructions are also possible to help the user hold the removal device, identify the best position on the actuation arms, and/or squeeze the device. For example, either or both actuation arms could have a texture to facilitate grasping and holding the removal device.

Figure 17:
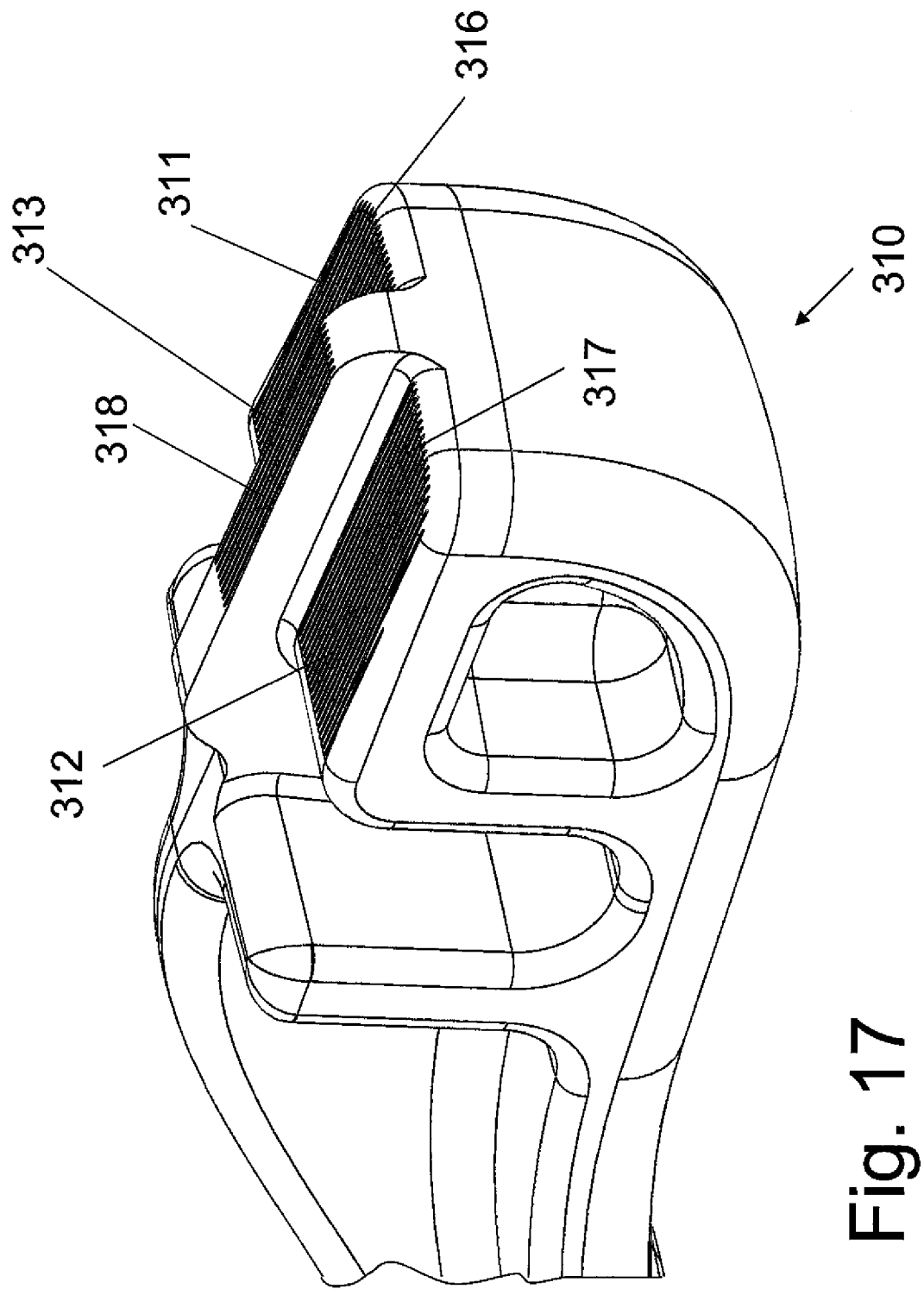
FIG. 17 is an enlarged perspective view of a portion of an alternate embodiment of a device of the present invention.

The removal devices of this invention can additionally or alternately include features to increase the engagement between the device and the backer being removed. For example, FIG. 17 illustrates a tip 310, which is similar to tip 33 from the embodiment shown in FIGS. 2 and 3. Tip 310 includes contact surfaces 311, 312 (similar to surfaces 76, 77 from the embodiment shown in FIGS. 2 and 3) and rib 313 (similar to rib 81 from the embodiment shown in FIGS. 2 and 3). Either or both contact surfaces 311, 312 and rib 313 includes friction-increasing feature(s) such as a suitable texture or the like. In this embodiment of FIG. 17, contact surfaces 311, 312 include a grip enhancing texture in the form of fine grooves 316, 317 respectively, and rib 313 includes a similar grip enhancing texture provided by fine grooves 318. Grooves 318 decrease the likelihood of a post slipping off from rib 313 during removal, as compared to a smooth-surfaced rib. Similarly, grooves 316, 317 increase the grip of surfaces 311, 312 against the backer loops (such as backer loops 6, 7, as illustrated in FIG. 5). Of course other friction-increasing features could alternately or additionally be used, features such as other physical features (e.g., bumps, indents, etc.) or friction-increasing coatings.

Advantageously, all of the embodiments described herein have features, geometry, and structure that allow the earring removal devices to be mass produced cost effectively. Preferred manufacturing methods for the main components include metal stamping and plastic molding.

The present invention has now been described with reference to several exemplary embodiments thereof. The entire disclosure of any patent or patent application identified herein is hereby incorporated by reference for all purposes. The foregoing disclosure has been provided for clarity of understanding by those skilled in the art of vacuum deposition. No unnecessary limitations should be taken from the foregoing disclosure. It will be apparent to those skilled in the art that changes can be made in the exemplary embodiments described herein without departing from the scope of the present invention. Thus, the scope of the present invention should not be limited to the exemplary structures and methods described herein, but only by the structures and methods described by the language of the claims and the equivalents of those claimed structures and methods.

What is claimed is:

1. A device for removing an earring held in position at least in part by a backer comprising first and second loops that have a spring force with an inward bias to grip a post of the earring, said device comprising:

a first tip and a second tip, wherein the first tip comprises a projecting rib that projects outward between first and second flat surfaces of the first tip, wherein the rib is positioned to press against and engage a tip of the earring post when the device engages the earring; and wherein the second tip comprises a backer engaging feature, wherein the backer engaging feature comprises a pair of projecting prongs that extend outward from the second tip and are configured in a manner effective to fit through and engage the first and second loops of the backer while the earring post projects through and is positioned between the pair of prongs, and wherein the projecting rib on the first tip and the prongs on the second tip are configured so that the projecting rib fits between the pair of projecting prongs when the projecting rib presses against the tip of the earring post during actuation while the pair of prongs engage the first and second loops of the backer; and an arcuate structure that couples the first tip to the second tip, said arcuate structure comprising a spring characteristic; wherein:

the spring characteristic is biased to cause the first and second tips to be separated from each other in a neutral position corresponding to an absence of a squeezing force applied to the arcuate coupling structure;

the first tip is able to engage the tip of the post during at least a portion of the time that the second tip engages the backer; and a first alignment feature located on the first tip and a second alignment feature located on the second tip, said alignment features cooperating to help the first and second tips move toward each other in a desired alignment during at least a portion of the time that the squeezing force is applied to the arcuate coupling structure; and wherein the first and second flat surfaces support the projecting rib and provide a backup function to engage and press against the tip of the earring post in case the earring post slips off the projecting rib; and wherein the arcuate structure is coupled to the first and second tips in a manner such that applying a squeezing force to the arcuate structure causes the first and second tips to move towards each other such that the projecting rib of the first tip engages and applies a force against the tip of the post of the earring and the prongs of the second tip engage and apply a force against the backer to help remove the backer from the earring post.

2. The device of claim 1, wherein the projecting rib comprises a friction-enhancing feature provided on a surface of the projecting rib that engages the tip of the post of the earring.

3. The device of claim 2, wherein the friction-enhancing feature comprises grooves on the surface of the projecting rib.

4. The device of claim 1, wherein the first and second alignment features comprise a pair of offset alignment posts on one of the first and second tips and a pair of offset alignment slots on the other of the first and second tips, wherein the offset alignment posts interface with the offset alignment slots during actuation.

5. The device of claim 1, wherein the first alignment feature comprises a slot and the second alignment feature comprises a post.

6. The device of claim 1, wherein the first alignment feature comprises a post and the second alignment feature comprises a slot.

7. The device of claim 1, wherein the first and second tips are continuous and integral with the arcuate structure coupled to the first and second tips.

\* \* \* \* \*